US00PP36534P2

(12) United States Plant Patent
Winslow

(10) Patent No.: US PP36,534 P2
(45) Date of Patent: Mar. 4, 2025

(54) ***PORTULACA* PLANT NAMED 'WGPORMM25'**

(50) Latin Name: *Portulaca oleracea*
Varietal Denomination: WGPORMM25

(71) Applicant: Benjamin K. Winslow, Austin, TX (US)

(72) Inventor: Benjamin K. Winslow, Austin, TX (US)

(73) Assignee: WENGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/755,586

(22) Filed: Jun. 26, 2024

(51) Int. Cl.
*A01H 5/02* (2018.01)
*A01H 6/00* (2018.01)

(52) U.S. Cl.
USPC ..... Plt./471

(58) Field of Classification Search
USPC ..... Plt./471
CPC ..... A01H 5/02; A01H 5/00; A01H 6/00
See application file for complete search history.

(56) References Cited

U.S. PATENT DOCUMENTS

PP31,187 P2 * 12/2019 Danziger ..... A01H 5/02
Plt./471

OTHER PUBLICATIONS

Danziger Pazzaz Nano Mango, retrieved on Sep. 30, 2024 at https://www.danzigeronline.com/catalog/annuals/pazzaz-nano-mango/, 7 pp. (Year: 2024).*
RHS *Portulaca oleracea* Pazzaz Nano Orange 'Dporpznorg' PBR (Pazzaz Series), retrieved on Sep. 30, 2024 at https://www.rhs.org.uk/plants/501020/portulaca-oleracea-pazzaz-nano-orange-(-dporpznorg-pbr)-(pazzaz-series)/details, one page. (Year: 2024).*

* cited by examiner

*Primary Examiner* — June Hwu
(74) *Attorney, Agent, or Firm* — C. Anne Whealy

(57) ABSTRACT

A new and distinct cultivar of *Portulaca* plant named 'WGPORMM25', characterized by its relatively compact, upright to outwardly spreading and mounding plant habit; vigorous growth habit and rapid growth rate; freely branching habit; dense and bushy appearance; early and freely flowering habit; long flowering period; golden orange-colored flowers with dark red-colored centers that remain open for an extended period of time during the daytime; and excellent container and garden performance.

1 Drawing Sheet

Botanical designation: *Portulaca oleracea.*
Cultivar denomination: 'WGPORMM25'.

BACKGROUND OF THE INVENTION

The present invention relates to a new and distinct cultivar of *Portulaca* plant, botanically known as *Portulaca oleracea*, commonly known as Common Purslane and hereinafter referred to by the name 'WGPORMM25'.

The new *Portulaca* plant is a product of a planned breeding program conducted by the Inventor in Alajuela, Costa Rica and Jacksonville, Texas. The objective of the breeding program is to create new vigorous *Portulaca* plants with numerous attractive flowers that remain open for an extended period of time during the daytime and are suitable as container and landscape plants.

The new *Portulaca* plant originated from a cross-pollination made by the Inventor in Alajuela, Costa Rica on Jun. 1, 2017 of *Portulaca oleracea* 'Campino Pitaya', not patented, as the female, or seed, parent with *Portulaca oleracea* 'SAKPOR003', disclosed in U.S. Plant Pat. No. 24,527, as the male, or pollen, parent. The new *Portulaca* plant was discovered and selected by the Inventor as a flowering plant from within the progeny of the stated cross-pollination in a controlled greenhouse environment in Jacksonville, Texas on Oct. 19, 2020.

Asexual reproduction of the new *Portulaca* plant by vegetative terminal cuttings in a controlled greenhouse environment in Jacksonville, Texas since Oct. 26, 2020, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WGPORMM25'. These characteristics in combination distinguish 'WGPORMM25' as a new and distinct *Portulaca* plant:

1. Relatively compact, upright to outwardly spreading and mounding plant habit.
2. Vigorous growth habit and rapid growth rate.
3. Freely branching habit; dense and bushy appearance.
4. Early and freely flowering habit.
5. Long flowering period.

6. Golden orange-colored flowers with dark red-colored centers that remain open for an extended period of time during the daytime.
7. Excellent container and garden performance.

Plants of the new *Portulaca* can be compared to plants of the female parent, 'Campino Pitaya'. Plants of the new *Portulaca* differ primarily from plants of 'Campino Pitaya' in the following characteristics:

1. Plants of the new *Portulaca* are more upright than and not as prostrate as plants of 'Campino Pitaya'.
2. Plants of the new *Portulaca* are more vigorous than plants of 'Campino Pitaya'.
3. Plants of the new *Portulaca* are more freely branching and are denser than plants of 'Campino Pitaya'.
4. Plants of the new *Portulaca* are more freely flowering than plants of 'Campino Pitaya'.
5. Flowers of plants of the new *Portulaca* remain open for a longer period of time during the daytime than flowers of plants of 'Campino Pitaya'.
6. Flowers of plants of the new *Portulaca* are golden orange in color with dark red-colored centers whereas flowers of plants of 'Campino Pitaya' are pinkish red and white bi- colored.

Plants of the new *Portulaca* can be compared to plants of the male parent, 'SAKPOR003'. Plants of the new *Portulaca* differ primarily from plants of 'SAKPOR003' in the following characteristics:

1. Plants of the new *Portulaca* are more upright than and not as mounding as plants of 'SAKPOR003'.
2. Plants of the new *Portulaca* are more vigorous than plants of 'SAKPOR003'.
3. Plants of the new *Portulaca* are more freely flowering than plants of 'SAKPOR003'.
4. Flowers of plants of the new *Portulaca* remain open for a longer period of time during the daytime than flowers of plants of 'SAKPOR003'.
5. Flowers of plants of the new *Portulaca* are golden orange in color with dark red-colored centers whereas flowers of plants of 'SAKPOR003' are pink in color.

Plants of the new *Portulaca* can be compared to plants of the *Portulaca oleracea* 'POR16000', disclosed in U.S. Plant Pat. No. 32,693. In side-by-side comparisons, plants of the new *Portulaca* differ primarily from plants of 'POR16000' in the following characteristics:

1. Plants of the new *Portulaca* are more upright than and not as prostrate as plants of 'POR16000'.
2. Plants of the new *Portulaca* are more vigorous than plants of 'POR16000'.
3. Plants of the new *Portulaca* have more flowers on the crown of the plant than plants of 'POR16000'.
4. Flowers of plants of the new *Portulaca* remain open for a longer period of time during the daytime than flowers of plants of 'POR16000'.
5. Flowers of plants of the new *Portulaca* are golden orange in color with dark red-colored centers whereas flowers of plants of 'POR16000' are dark red in color.

Plants of the new *Portulaca* can also be compared to plants of the *Portulaca oleracea* 'Dporpznorg' (U.S. Plant Pat. No. 31,187) also known as Pazzaz Nana Orange. In side-by-side comparisons, plants of the new *Portulaca* differ primarily from plants of 'Dporpznorg' in the following characteristics:

1. Plants of the new *Portulaca* are more upright than plants of 'Dporpznorg'.
2. Plants of the new *Portulaca* are more vigorous than plants of 'Dporpznorg'.
3. Flowers of plants of the new *Portulaca* remain open for a longer period of time during the daytime than flowers of plants of 'Dporpznorg'.
4. Flowers of plants of the new *Portulaca* are golden orange in color with dark red-colored centers whereas flowers of plants of 'Dporpznorg' are light orange in color with yellow-colored centers.

BRIEF DESCRIPTION OF THE PHOTOGRAPH

The accompanying colored photograph illustrates the overall appearance of the new *Portulaca* plant showing the colors as true as it is reasonably possible to obtain in colored reproductions of this type. Colors in the photograph may differ slightly from the color values cited in the detailed botanical description which accurately describe the colors of the new *Portulaca* plant.

The photograph is a side perspective view of a typical flowering plant of 'WGPORMM25' grown in a container.

DETAILED BOTANICAL DESCRIPTION

The aforementioned photograph and following observations and measurements describe plants grown during the late winter and early spring in 10.75-cm containers in a glass-covered greenhouse in Loudon, New Hampshire and under cultural practices typical of commercial *Portulaca* production. During the production of the plants, day and night temperatures averaged 20° C. Plants were eight weeks from planting rooted young plants when the photograph was taken and ten weeks from planting when the detailed description was taken. In the following description, color references are made to The Royal Horticultural Society Colour Chart, 2015 Edition, except where general terms of ordinary dictionary significance are used.

Botanical classification: *Portulaca oleracea* 'WGPORMM25'.

Parentage:

*Female, or seed, parent.*—*Portulaca oleracea* 'Campino Pitaya', not patented.

*Male or pollen parent.*—*Portulaca oleracea* 'SAKPOR003', disclosed in U.S. Plant Pat. No. 24,527.

Propagation:

*Type.*—By vegetative terminal cuttings.

*Time to initiate roots, summer.*—About three to four days at ambient temperatures about 28° C.

*Time to initiate roots, winter.*—About five to seven days at ambient temperatures about 20° C.

*Time to produce a rooted young plant, summer.*—About three to four weeks at ambient temperatures about 28° C.

*Time to produce a rooted young plant, winter.*—About four to five weeks at ambient temperatures about 20° C.

*Root description.*—Fine, fleshy; typically white in color, actual color of the roots is dependent on substrate composition, water quality, fertilizers, substrate temperature and age of roots.

*Rooting habit.*—Freely branching; medium density.

Plant description:

*Plant and growth habit.*—Relatively compact, upright to outwardly spreading and mounding plant habit;

vigorous growth habit and rapid growth rate; freely branching habit; dense and bushy appearance.

*Branching habit*.—Freely branching habit about seven to ten primary lateral branches per plant each with secondary lateral branches developing potentially at every node; pinching enhances branching potential.

*Plant height*.—About 10 cm to 12 cm.

*Plant diameter* (*area of spread*).—About 34 cm.

Lateral branch/peduncle description:

*Length*.—About 22 cm to 25 cm.

*Diameter*.—About 3 mm to 3.25 mm.

*Internode length*.—Variable, about 1.2 cm to 1.8 cm.

*Strength*.—Moderately strong; flexible.

*Texture and luster*.—Smooth, glabrous; moderately glossy.

*Color, developing*.—Close to between 146A and 148A variably overlain with close to 59A.

*Color, developed*.—Close to 59A.

Leaf description:

*Arrangement*.—Opposite, simple.

*Length*.—About 2.2 cm to 2.5 cm.

*Width*.—About 9 mm to 10 mm.

*Shape*.—Narrowly obovate.

*Apex*.—Acute to acuminate.

*Base*.—Cuneate to attenuate.

*Margin*.—Entire.

*Texture and luster, upper and lower surfaces*.—Smooth, glabrous; fleshy, succulent; moderately glossy.

*Venation pattern*.—Pinnate.

*Color*.—Developing leaves, upper surface: Close to 146A. Developing leaves, lower surface: Close to 146A to 146B. Fully expanded leaves, upper surface: Close to 147A; midvein proximally, close to between 144A and 146B; midvein distally and lateral venation, close to 147A. Fully expanded leaves, lower surface: Close to 138A; midvein proximally, close to 144A; midvein distally and lateral venation, close to 138A.

*Petioles*.—Length: About 1 mm to 2 mm. Diameter: About 1 mm to 2 mm. Texture and luster, upper and lower surfaces: Smooth, glabrous; semi-glossy. Strength: Moderately strong. Color, upper and lower surfaces: Close to 144A.

Flower description:

*Flower arrangement*.—Single rotate and cupped flowers; freely flowering habit with about three to five flowers per terminal; numerous flowers developing continuously per plant during the flowering season; flowers face mostly upright to slightly outwardly.

*Fragrance*.—None detected.

*Natural flowering season*.—Plants begin flowering about seven weeks after planting; in the garden, plants flower continuously from spring until autumn in New Hampshire.

*Flower longevity*.—Depending on temperature, flowers last about one to three days on the plant; flowers not persistent; flowers remain open for an extended period of time during the daytime.

*Flower buds*.—Length: About 9 mm to 10 mm. Diameter: About 4 mm to 5 mm. Shape: Narrowly ovoid. Texture and luster: Smooth, glabrous; moderately glossy. Color, developing sepals: Close to 137A to 137B.

*Flower diameter*.—About 2.6 cm to 2.8 cm.

*Flower length* (*height*).—About 1 cm to 1.2 cm.

*Petals*.—Quantity per flower: Corolla consists of five petals fused at the base. Length: About 1.2 cm to 1.3 cm. Width: About 1.1 cm to 1.25 cm. Shape: Obcordate. Apex: Emarginate and occasionally with cuspidate apex. Base: Fused. Margin: Entire, slightly to moderately undulate and slightly reflexing with development. Texture and luster, upper surface: Smooth, glabrous, satiny; moderately glossy. Texture and luster, lower surface: Smooth, glabrous; moderately glossy. Color: When opening, upper surface: Close to 16A; towards the base, close to 53A. When opening, lower surface: Close to 16B to 16C; towards the base, close to 53A. Fully opened, upper surface: Close to 16A to 16B iridescent; towards the base, close to 53A; venation, similar to lamina colors; colors do not change with subsequent development. Fully opened, lower surface: Close to 16B to 16C; towards the base, close to 53A; venation, similar to lamina colors; colors do not change with subsequent development.

*Sepals*.—Quantity per flower: Two fused into a tubular calyx. Length: About 7 mm to 8 mm. Width: About 3.5 mm to 4 mm. Shape: Ovate. Apex: Acute to acuminate. Margin: Entire. Texture and luster, upper surface: Smooth, glabrous; moderately glossy. Texture and luster, lower surface: Smooth, glabrous; slightly glossy. Color, upper surface: Close to 144A, translucent. Color, lower surface: Close to 137A to 137B, translucent.

*Reproductive organs*.—Androecium: Quantity of stamens per flower: About 12 to 16. Filament length: About 3.5 mm to 4 mm. Filament color: Close to 9A variably tinged with close to 53A. Anther shape: Oblong. Anther length: Less than 1 mm. Anther color: Close to 21B. Amount of pollen: None observed. Gynoecium: Pistil length: About 8 mm. Style length: About 6 mm. Style color: Close to 53B to 53C. Stigma diameter: About 5 mm. Stigma shape: Four-parted. Stigma color: Close to 50A. Ovary color: Close to 144A. Fruits and seeds: To date, fruit and seed development have not been observed on plants of the new *Portulaca*.

Garden performance: Plants of the new *Portulaca* have been observed to have excellent garden performance and to tolerate temperatures ranging from about 2° C. to about 40° C.

Pathogen & pest resistance: To date, plants of the new *Portulaca* have not been shown to be resistant to pathogens and pests common to *Portulaca* plants.

It is claimed:

1. A new and distinct *Portulaca* plant named 'WGPORMM25' as herein illustrated and described.

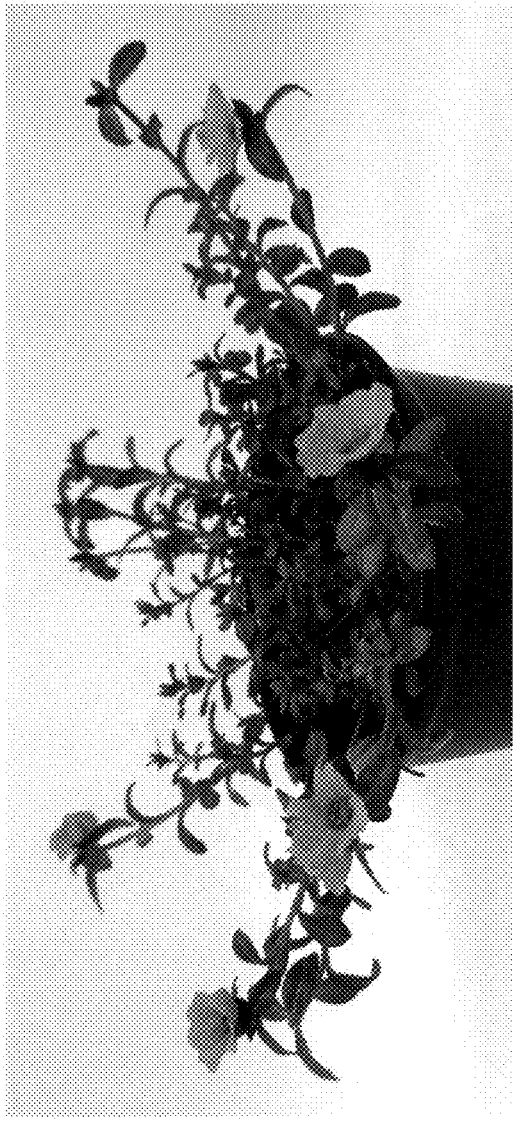

* * * * *